United States Patent [19]

Petrignani

[11] Patent Number: Plant 6,338

[45] Date of Patent: Oct. 18, 1988

[54] EARLY-RIPENING "RIPETRI" VARIETY OF CLEMENTINE TANGERINE

[76] Inventor: Michel Petrignani, Domaine de Cento Chiave, 20290 Borgo, Corse, France

[21] Appl. No.: 823,354

[22] Filed: Jan. 28, 1986

[30] Foreign Application Priority Data

Jan. 31, 1985 [FR] France ..... 85 01482

[51] Int. Cl.[4] ..... A01H 5/03

[52] U.S. Cl. ..... Plt./45

[58] Field of Search ..... Plt. 45

*Primary Examiner*—Robert E. Bagwill

*Attorney, Agent, or Firm*—William H. Elliott, Jr.; William T. King

[57] ABSTRACT

A new variety of Clementine tangerine named "Ripetri", the principal characteristics of which lie its abundant production of early ripening seedless fruit. The shrubby development of the new variety makes it particularly well suited for dense field cultivation or dwarfed for potted shrub use.

5 Drawing Sheets

This invention relates to a new variety of Clementine tangerine cv. Ripetri, distinguishable from known varieties by the following combination of characteristics:

The new variety is everblooming and extremely fruitful from its youngest age; the fruit is endowed with pleasing organoleptic qualities and delicate flavor; fruit are aspermous (lacking seeds); the peel of the fruit is thinner than that of known varieties; and the shrubby development is smaller than in the case of known varieties — making this variety particularly well suited for controlled nanization i.e. (artificial dwarfing) and growth in pots.

Under growing conditions prevailing in Corsica, France, the fruit of the new variety ripens in about six weeks after pollination; thus the "Ripetri" tangerine ripens about 15 days to 3 weeks earlier than other known varieties grown under similar conditions.

The goal of the applicants was to create a Clementine tangerine variety that would possess the above-mentioned qualities and advantages expressed from a combination of parental genes. Previous study of the inheritability of the sought characteristics permitted prediction of their expression in later generations.

The new variety is a descendant of repeated pollination of unnamed mutations of Messerghin-type Clementine tangerine, conducted over a ten year period.

The male parent was a seeded tangerine variety; the female parent was a seedless tangerine variety.

The artificial fertilization process used by the applicants is explained by the following formula: R 210 (with seeds)×R 107 (without seeds).

Hybridization resulted in several hundreds of seeds, the cells of which contained a combination of factors existing in the cells of the parents.

Hundreds of seeds were sown, each growing into a seedling biologically distinct from every other seedling.

After discarding all deficient seedlings, or those seedlings in which the characteristics deviated from those being the object of the research, applicants proceeded to a second stage of experimentation. Trees grown from selected seedlings eventually permitted the selection of two varieties which were then asexually propagated and grown in Figueretto and Casamozza (Corsica) for a 10 year period of observation.

At the end of the 10-year period of observation, applicants selected the one variety which presented a set of characteristics coming closest to the desired goal. This variety was named "Ripetri". Technical tests were then made on the "Ripetri" variety to verify its behavior, its morphological characteristics, as well as its fruit-bearing aptitude.

Flowering of the new variety takes place during several, usually four, periods of the year. However, this characteristic may be modified in dense field cultivation by means of various known agricultural techniques resulting in a single, short-cycle, spring flowering.

The shorter physiological cycle of about 3 weeks in relation to known varieties enables a characteristic early maturity leading to the harvesting of fruit 3 to 4 weeks before other known varieties. This early maturity can vary with the cultivation region.

The physiological characteristics of the "Ripetri" variety enables a certain aptitude toward controlled nanization, i.e., dwarfing. Such dwarf plants, when potted, are capable of achieving all stages of the plant cycle: flowering, fructification, ripening.

Furthermore, it should be noted that, under normal cultivation conditions, the early flowering occurs in the same year as the grafting. This flowering is followed systematically by the development and ripening of the fruit. The absence of physiological falling, (i.e. immature fruit dropping off the tree before ripening) usual with other Clementine tangerines, results in higher yields of fruit.

The particular strength of the new variety, explaining its high yield, is observed by a swelling of the grafting characteristic on certain rootstock, for example, "bigaradier" (bitter orange-tree).

The productivity of the new variety was widely tested. The results emphasize the importance of the creation of such a variety, in view of its industrial use by professionals in the citrus industry for the production of a new variety of Clementine tangerine.

The characteristics and properties of the new variety, obtained as indicated above, are rigorously transmissible by vegetative (or asexual) means, that is, by any means of vegetative reproduction.

The new variety will be marketed under the name of "Ripetri". The new Clementine tangerine variety, subject of the present application, retains its essential characteristics through repeated asexual propagation by budding. Botanical and descriptive characteristics of plants of the new variety grown in Corsica, France are listed below and are believed to apply to plants grown under similar conditions of soil and climate elsewhere.

BRIEF DESCRIPTION OF THE DRAWING

In order to further identify and characterize the new variety, photographs described below illustrate distinctive elements of the new variety.

DESCRIPTION

Figure 1:
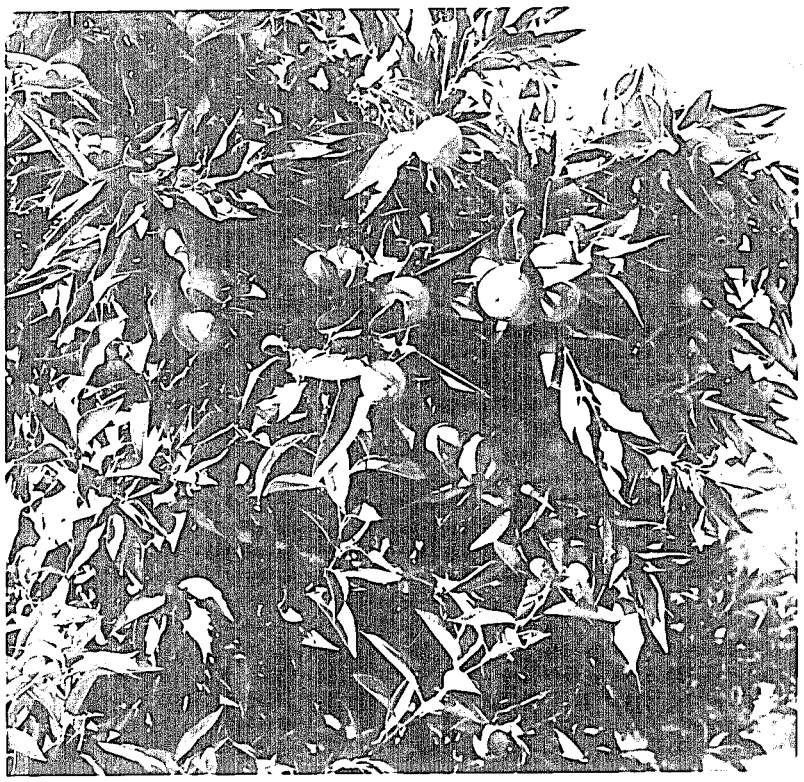
FIG. 1: Photograph showing a one year graft with apical fruit.
Figure 2:
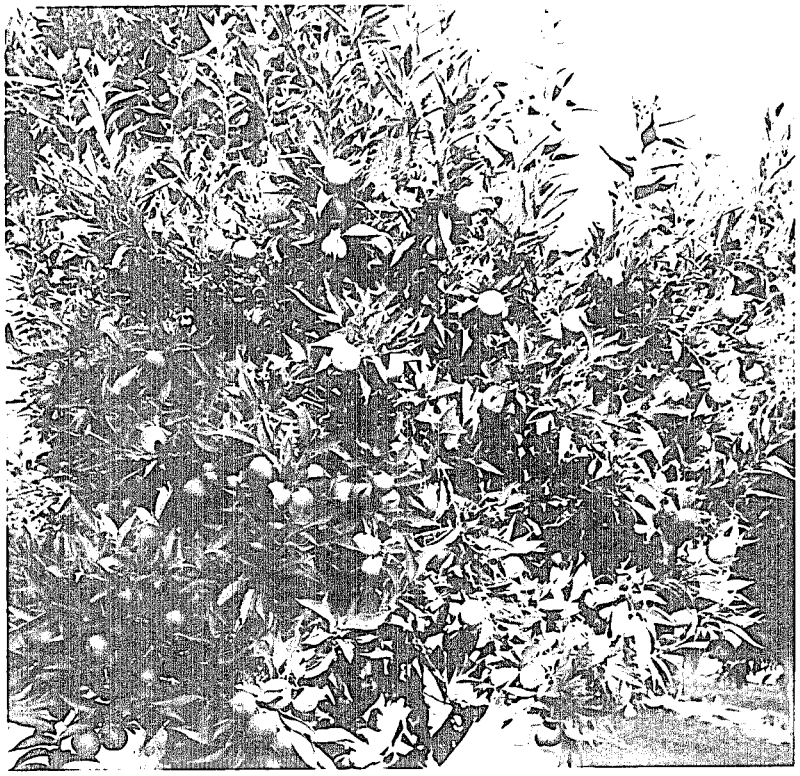
FIG. 2: Photograph showing two year graft.
Figure 3:
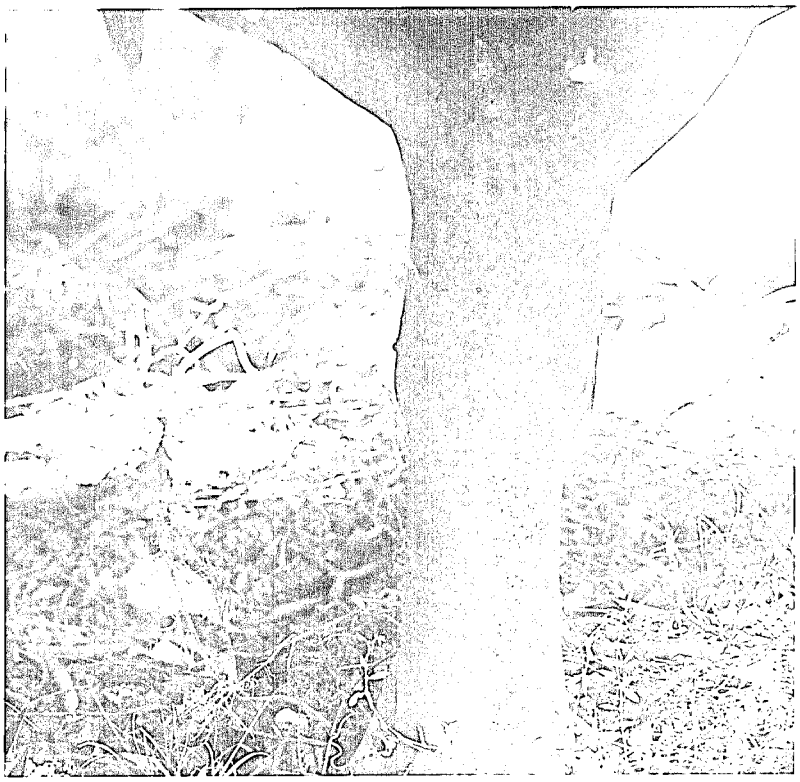
FIG. 3: Photograph showing swelling of graft on "Bigaradier" (bitter orangetree)
Figure 4:
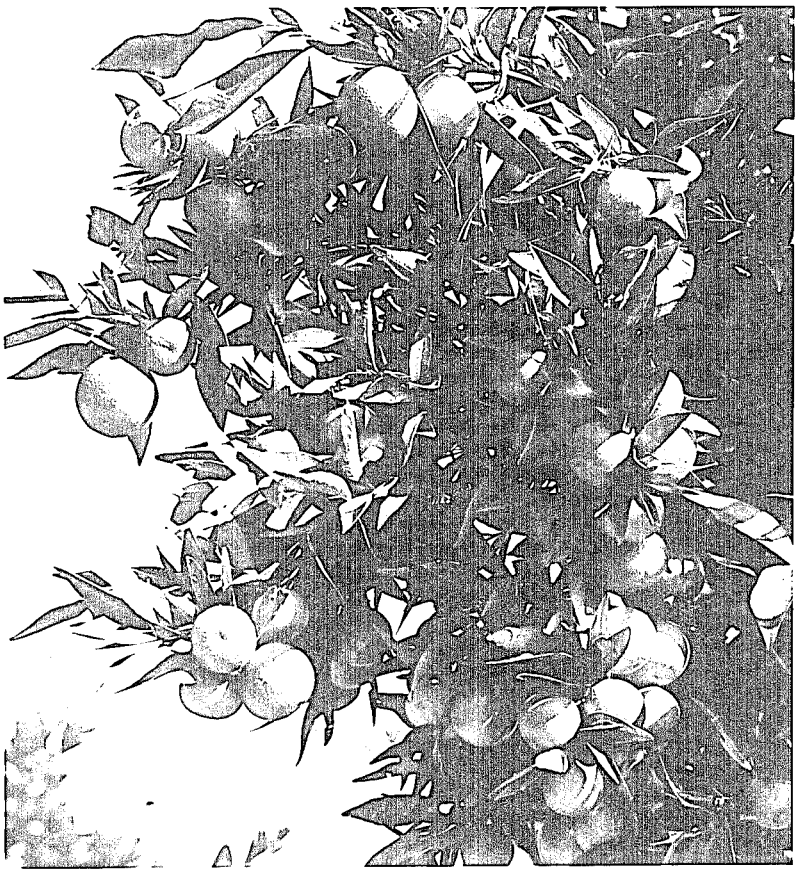
FIG. 4: Photograph showing fruit at maturity.
Figure 5:
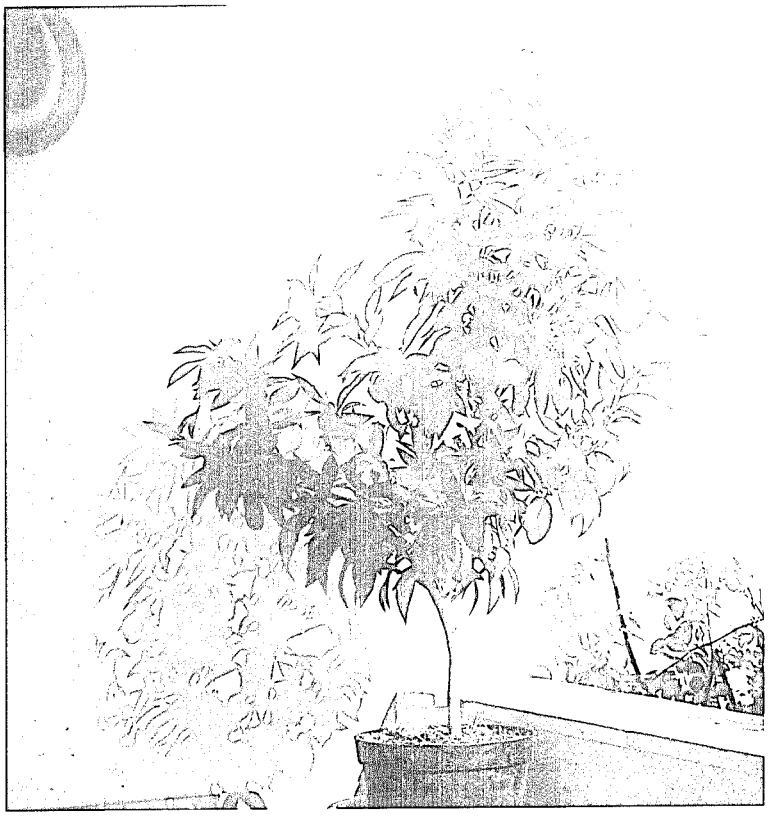
FIG. 5: Photograph showing dwarf potted plant.
Figure 6:
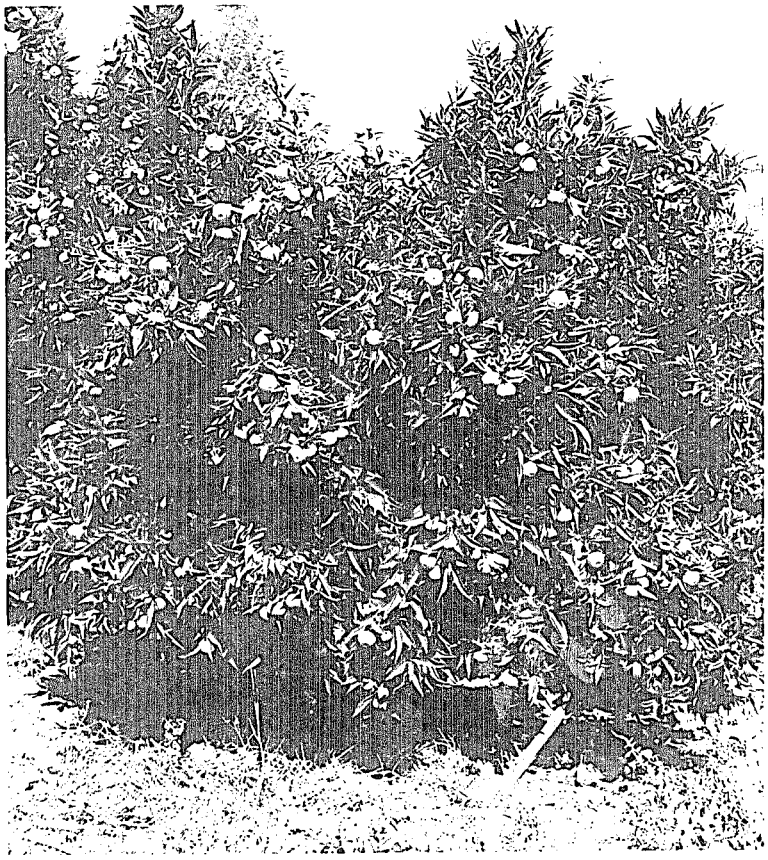
FIG. 6: Photograph showing standard tree in production (5 year graft)
Figure 7:
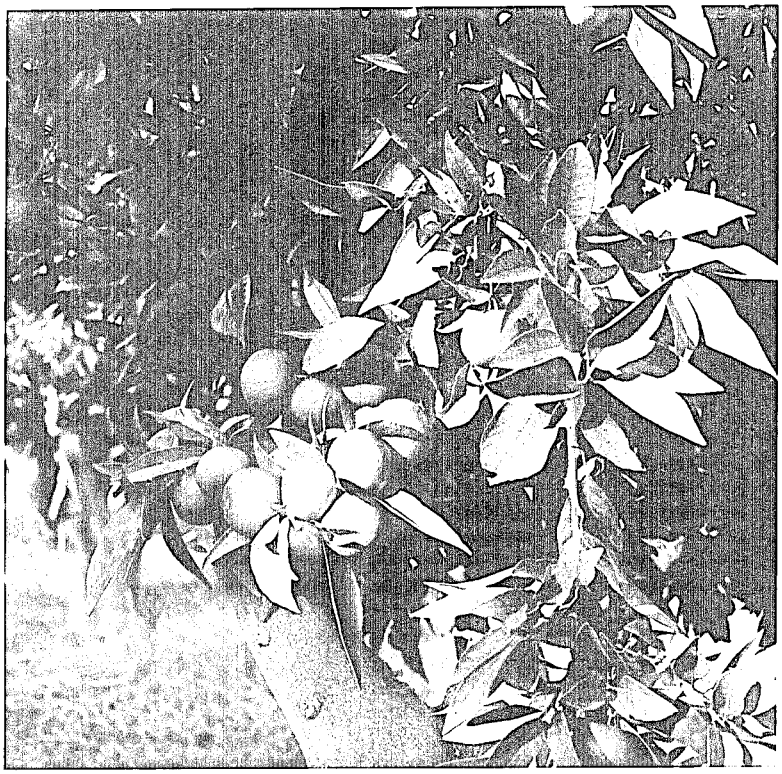
FIG. 7: Photograph showing cluster effect.
Figure 8:
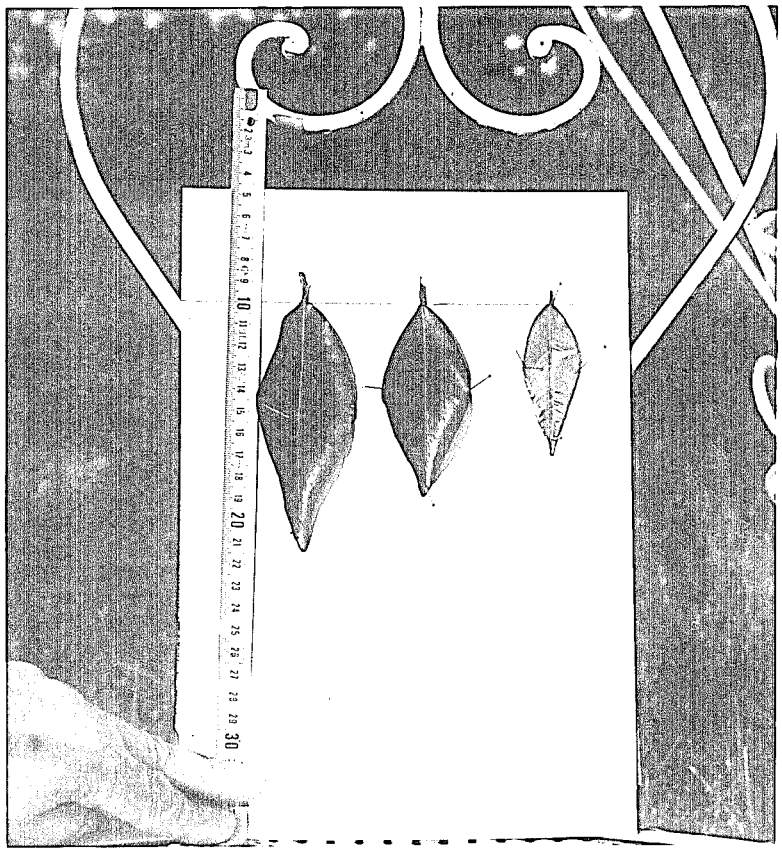
FIG. 8: Photograph showing leaves with centimeter scale.
Figure 9:
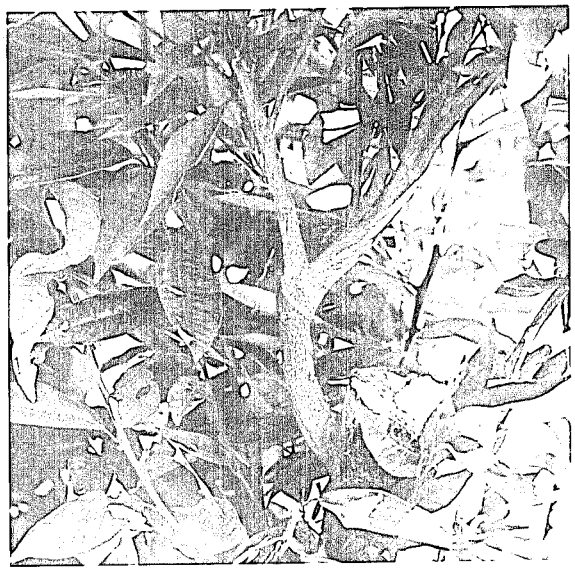
FIG. 9: Photograph showing swelling of graft.

Plants of the new variety generally reach 2 meters in height at maturity.

Branches are upright. Leaf petioles are straight and slightly adnate. Petioles of young leaves are about 5 mm in length; petioles of adult leaves are about 15 mm in length.

Leaflets are numerous and oval in shape, without indentation. Leaflets are coriaceous in texture and have a glazed epidermis. Leaflets are pale green, becoming a darker green as the leaf matures.

Young leaves are smooth with a glazed epidermis on their upper surface. The lower leaf surface is dull in color, having slightly protuberant ribs. Young leaves are about 7 cm in length, having a median width of about 2 cm.

Adult leaves are smooth and tough and dark green on their upper surface. The lower adult leaf surface is dull in color, oval in shape having protuberant ribs. Adult leaf size is approximately 11 cm in length, 4 cm in median width.

FLOWER

Anthocyanin coloration of the terminal flower bud, when the petal tips are just visible, is absent. Stamens are medium in number. Development of the style is complete. Anther color is white. Clusters of flowers occur more than once.

FRUIT

Fruit of the new variety are of medium size and oblate in shape. The basal end of the fruit is moderately depressed; the distal end is truncate.

The surface of the fruit is orange in color, smooth in texture with dense and conspicuous rind glands. A navel is absent or at least very rare. The rind is thin to medium in thickness and adheres to the flesh weakly to medium in strength. The albedo of the fruit is white. Flesh is uniformly orange in color in cross section. The columella is semi-hollow and small in diameter. The fruit has a medium number of segments. Fruit is medium juicy; the juice is orange in color and of low acid content. Fruit juice contains a medium quantity soluble solids. Fruit fiber is of medium strength. Polyembryonic seeds are absent.

DEVELOPMENT

The simultaneous development of the terminal shoot and the axillary shoots gives the plant sympodial growth.

The flowering at the apex of yearly growth represents a very high proportion of the total flowering.

Regardless of the climatic, agricultural and cultivating conditions, a normal development of the flower up to the ripening of the fruit takes place in the absence of any crop failures, for example, (due to washing away of pollen by rain), or physiological falling during development. This characteristic requires the mastery of the size and cultivating techniques (water and fertilization).

I claim:

1. A new variety of Clementine tangerine cv. Ripetri and the parts thereof, substantially characterized as shown and described herein, by its everblooming and extremely fruitful characteristic from its youngest age; early ripening fruit endowed with pleasing organoleptic qualities; thin to medium thick skin and total aspermatism; and its suitability for dense field cultivation and dwarfing for potted use.

* * * * *